(12) United States Patent
Smith et al.

(10) Patent No.: US 9,433,942 B2
(45) Date of Patent: Sep. 6, 2016

(54) BIOLOGICAL SAMPLE STORAGE DEVICE

(75) Inventors: Michael John Smith, Cardiff (GB); Stevan Paul Tortorella, Wells, ME (US); Gerard B. O'Beirne, Cardiff (GB)

(73) Assignee: GE HEALTHCARE UK LIMITED, Little Chalfont (GB)

( * ) Notice: Subject to any disclaimer, the term of this patent is extended or adjusted under 35 U.S.C. 154(b) by 0 days.

(21) Appl. No.: 13/990,144

(22) PCT Filed: Nov. 24, 2011

(86) PCT No.: PCT/EP2011/070958
§ 371 (c)(1),
(2), (4) Date: May 29, 2013

(87) PCT Pub. No.: WO2012/072495
PCT Pub. Date: Jun. 7, 2012

(65) Prior Publication Data
US 2013/0260477 A1 Oct. 3, 2013

(30) Foreign Application Priority Data

Nov. 29, 2010 (GB) .................................. 1020174.7

(51) Int. Cl.
*B01L 9/00* (2006.01)
*B01L 3/00* (2006.01)
(Continued)

(52) U.S. Cl.
CPC .................. *B01L 3/508* (2013.01); *B01L 9/52* (2013.01); *B01L 2200/025* (2013.01);
(Continued)

(58) Field of Classification Search
CPC ....................................................... B01L 3/508

USPC .......................... 436/174, 176; 422/547, 554
See application file for complete search history.

(56) References Cited

U.S. PATENT DOCUMENTS 4,230,757 A 10/1980 Toner
4,440,301 A 4/1984 Intengan
(Continued)

FOREIGN PATENT DOCUMENTS

DE 102 45 961 4/2004
DE 10245961 B4 * 7/2007 ................ B01L 9/06
(Continued)

OTHER PUBLICATIONS

English Machine Translation of Gora (DE 102 45 961 B4) obtained Jul. 29, 2015.*
(Continued)

*Primary Examiner* — Christopher A Hixson
*Assistant Examiner* — Emily Berkeley
(74) *Attorney, Agent, or Firm* — Sutherland Asbill & Brennan LLP

(57) ABSTRACT

Apparatus for holding biological samples and methods of assembling the same are disclosed. In an embodiment, a pair of rigid frames is described, each frame comprising an aperture. A biological sample storage medium is placed between the two frames so that the biological sample storage medium at least partly overlaps each of the apertures in the frames. The two frames are joined to fix the biological sample storage medium in place while allowing access to the biological sample storage medium via each of the apertures. The frames can be rigid and waterproof, and provide a robust storage media for biological samples. At least one pre-defined area of weakness can be provided in the frames, to allow removal of a portion of the frames, which may correspond to indicia on the storage medium.

21 Claims, 10 Drawing Sheets

(51) Int. Cl.
 *G01N 35/00* (2006.01)
 *G01N 1/31* (2006.01)

(52) U.S. Cl.
 CPC ....... *B01L 2200/12* (2013.01); *B01L 2300/02* (2013.01); *B01L 2300/069* (2013.01); *B01L 2300/0819* (2013.01); *B01L 2300/0822* (2013.01); *G01N 1/312* (2013.01); *G01N 35/00732* (2013.01); *Y10T 436/25* (2015.01)

(56) References Cited

U.S. PATENT DOCUMENTS

| | | | |
|---|---|---|---|
| 4,668,472 A | | 5/1987 | Sakamoto |
| 4,735,778 A | | 4/1988 | Maruyama |
| 5,292,000 A | * | 3/1994 | Levy ............................ 206/456 |
| 6,376,233 B1 | | 4/2002 | Wolf et al. |
| 2003/0168600 A1 | * | 9/2003 | Tseng et al. ............. 250/339.07 |
| 2004/0141884 A1 | * | 7/2004 | Unno et al. ................... 422/100 |
| 2004/0151637 A1 | | 8/2004 | Davin |
| 2004/0265187 A1 | | 12/2004 | Davin |
| 2006/0210451 A1 | | 9/2006 | Anderson |
| 2009/0117011 A1 | | 5/2009 | Morrison |

FOREIGN PATENT DOCUMENTS

| | | | |
|---|---|---|---|
| EP | 1 445 021 | | 8/2004 |
| EP | 1445021 A1 * | 8/2004 | ............... B01L 3/00 |
| EP | 1 772 735 | | 4/2007 |
| WO | WO 01/90729 | | 11/2001 |
| WO | WO 2010/079223 | | 7/2010 |

OTHER PUBLICATIONS

Japanese Office Action for JP Application No. 2013-541301 mailed Dec. 1, 2015 (6 pages).

* cited by examiner

BIOLOGICAL SAMPLE STORAGE DEVICE

CROSS-REFERENCE TO RELATED APPLICATIONS

This application is a filing under 35 U.S.C. 371 of international application Number PCT/EP2011/070958, filed Nov. 24, 2011, published on Jun. 7, 2012 as WO 2012/072495, which claims priority to patent application No. 1020174.7 filed in Great Britain on Nov. 29, 2010.

FIELD OF THE INVENTION

The present invention relates to a device for storing and holding biological samples, to a method of assembling a device for storing and holding a biological sample, and a method of analysing a biological sample using the device.

BACKGROUND OF THE INVENTION

Biological samples, such as blood samples taken for drug discovery and saliva taken for DNA profiling in criminal investigations, are typically manually collected and placed on an absorbent storage medium, which may comprise a membrane impregnated with chemicals for stabilising the sample. The samples are allowed to dry and, once dry, the biological storage medium can be transported to a testing facility for analysis.

Such biological storage media are typically delicate, and require some kind of protective casing for handling and storage. Conventionally, such cases have been constructed of relatively thin, flexible cardboard; however, such cardboard cases suffer from a number of drawbacks. Firstly, cardboard is susceptible to damage by moisture; the constituent components of a cardboard case are likely to warp or even delaminate if the device comes into contact with water. Secondly, cardboard has a relatively low structural strength; rough handling during transport is likely to result in bending, tearing or crushing of the cardboard case. These defects may present problems in subsequent handling. For example, if the sample stored is a test sample, tests may be carried out using robotic or other automated handling systems. If, however, the storage medium and/or the protective case in which it is stored is not flat or is otherwise damaged, this may cause problems for the automatic handling system.

US20090117011A1 proposes a rigid holder into which the sample card and cardboard case may be inserted to protect it from mechanical damage during transportation. The construction of the device is such that it is also resistant to water to prevent it from warping if it gets wet. However, the rigid holder adds an additional structure to the sample storage device, making it complicated and expensive to manufacture and assemble. Further, the cardboard case and sample storage medium are simply inserted into the rigid holder by aligning the sample card with a groove in the rigid holder; this means that the cardboard case and sample card can easily be removed, or simply fall out during automated or other handling of the device; this may lead to samples being inadvertently misplaced or misdirected, with obvious undesirable consequences.

It is an object of the present invention to at least mitigate the problems of the prior art.

In addition, the device of the present invention is, not exclusively, intended for use with an automated punching system which will remove a piece of sample storage medium. Therefore, the device has to be rigid but the sample storage medium has to be assessable to the punching system.

Since automated processing of the manually collected sample is envisaged, the need for communicating incorrect/insufficient/contaminated placement of the sample on the medium is desirable.

SUMMARY OF THE INVENTION

In accordance with a first aspect of the present invention, there is provided a method of assembling a device for storing and holding a biological sample, the method comprising: providing a first rigid frame, the first rigid frame comprising a first aperture; placing a biological sample storage medium onto the first rigid frame so that the biological sample storage medium at least partly overlaps said first aperture; placing a second rigid frame comprising a second aperture onto the first rigid frame such that the first and second rigid frames enclose the biological sample storage medium, the second rigid frame being placed such that the second aperture at least partly overlaps the biological sample storage medium; and attaching the first rigid frame to the second rigid frame, thereby holding the biological sample medium between the first rigid frame and the second rigid frame, whereby the biological sample storage medium is accessible via each of said first aperture and said second aperture, the method being characterised in that the first and/or second frame includes least one pre-defined area of weakness for allowing a portion of said frame to be manually removed.

By sandwiching the biological sample medium between two rigid frames, a sample holding device can be formed which is easily handled, and is robust against damage during handling. Fixing the sample storage medium between the two rigid frames protects it against inadvertent removal and/or falling out of the frames provided.

Further, since the rigid frames are applied directly to the biological sample storage medium itself, the device is simple, involving relatively few components. Thus, manufacturing and assembly of the device are efficient.

Preferably, a recess is provided in at least one of the first rigid frame and the second rigid frame, the recess having dimensions arranged to correspond with the biological sample storage medium, the method comprising locating the biological sample storage medium in said recess. Additionally, or alternatively, the method may comprise attaching the biological storage medium to at least one of the first rigid frame and the second rigid frame using an adhesive. Alternatively, or additionally, the at least one of the first rigid frame and the second rigid frame is provided with at least one stake, and the biological sample storage medium is provided with at least one hole, where the number and positions of at least one of the holes corresponds to the number and positions of at least one of the stakes, and the method comprises: locating the at least one stake in the at least one hole; and performing a heat and/or pressure deformation process to deform the at least one stake such that the deformed stake prevents removal of the biological sample storage medium from the first and/or second rigid frame.

These features provide convenient ways of locating the biological sample storage medium within the first and second rigid frames.

In some embodiments, one of the first and second rigid frames comprises at least one boss and the other of the rigid frames comprises at least one hole, and the position of the at least one hole corresponds to the position of the at least one boss, the method comprising locating the at least one boss within the at least one hole to align the first rigid frame with the second rigid frame. This provides a convenient way of correctly aligning the two rigid frames together.

In accordance with another aspect of the present invention, there is provided a device for holding a biological sample, the device comprising: a biological sample storage medium; a first rigid frame comprising a first aperture, the first aperture at least partly overlapping the biological sample storage medium; and a second rigid frame comprising a second aperture, the second aperture at least partly overlapping the biological sample storage medium, wherein the biological sample storage medium is fixed between the first rigid frame and the second rigid frame, and the biological sample storage medium is accessible via each of said first aperture and said second aperture, and wherein the first and/or second frame includes least one pre-defined area of weakness for allowing a portion of said frame to be manually removed.

In accordance with an alternative embodiment of the invention, there is provided a device for holding a biological sample, the device comprising: a biological sample storage medium; a first rigid frame comprising a first aperture, the first aperture at least partly overlapping the biological sample storage medium; and a second rigid frame comprising a second aperture, the second aperture at least partly overlapping the biological sample storage medium, wherein the biological sample storage medium is fixed between the first rigid frame and the second rigid frame, and the biological sample storage medium is accessible via each of said first aperture and said second aperture, and wherein the first and/or second frame includes least one notch formed in the periphery of said first and/or second frames.

In some embodiments, the biological sample medium includes a plurality of pre-defined areas for storing a biological sample, and said areas of weakness in at least one of the first or second rigid frames comprises a plurality of removable parts located at positions corresponding to the pre-defined areas. This enables unusable samples to be reliably indicated by removing a part in a position corresponding to an unusable sample.

In some embodiments, an outer surface of at least one of the first rigid frame and second rigid frame comprises a textured portion. Alternatively, or additionally, an outer surface of at least one of the first and second rigid frames may comprise at least one recess, the at least one recess having a size and shape corresponding to that of an end effector of an automated handling system. These features improve the ease of handling of the device.

In accordance with yet another aspect of the present invention, there is provided apparatus for storing biological samples, the apparatus comprising: a magazine comprising a plurality of slots for holding a plurality of devices according to the second aspect of the present invention, the devices each including a notch located on an outside edge of the device; and a plurality of devices according to the second aspect of the present invention, wherein each said slot comprises a protrusion having dimensions arranged to correspond to dimensions of said at least one notch.

These features enable multiple devices to be reliably stored in a predetermined orientation.

A method of analysing a biological sample employing the device mentioned above is contemplated.

Further features and advantages of the invention will become apparent from the following description of preferred embodiments of the invention, given by way of example only, which is made with reference to the accompanying drawings.

DETAILED DESCRIPTION OF THE INVENTION

Figure 1A:
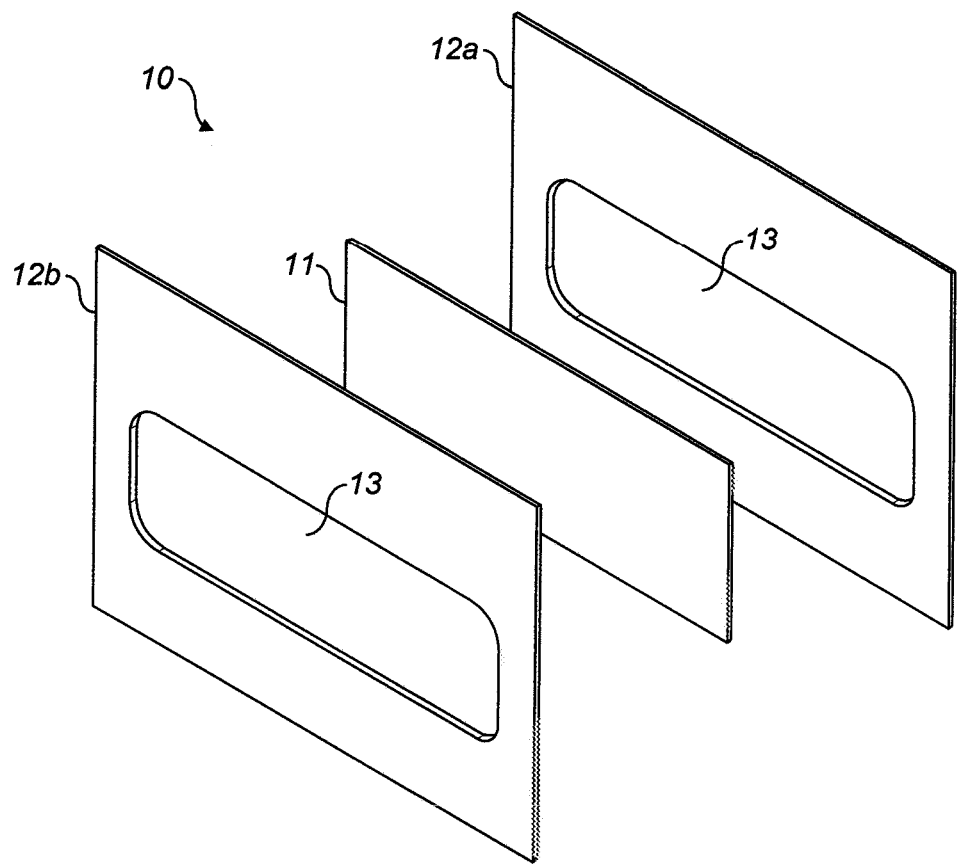
FIG. 1a shows a perspective exploded view of a device for holding a biological sample according to a first embodiment of the present invention.

FIG. 1a shows a biological sample holder 10 according to an exemplary embodiment of the present invention. The biological sample holder 10 comprises a biological sample storage medium 11 disposed between two rigid (i.e. resistant to deformation under the application of a mechanical force), substantially flat frames 12a and 12b. The frames 12a, 12b each contain an aperture 13, (which will be referred to hereafter as a "window") such that the biological sample storage medium 11 is accessible to a user from either side of the device 10.

The frames 12a, 12b may be manufactured from a plastics material using an injection moulding process. The plastics material used should be selected such that it does not easily deform when exposed to moisture, or externally applied mechanical forces, and may be selected to withstand high temperatures or pressures. This makes the sample holder 10 particularly suited to automated (e.g. robotic) processing, since the sample holder 10 should substantially remain rigid and flat, allowing precision robotic removal and replacement of the samples from and to sample handling magazines, for example. The plastics material may also be selected such that it does not easily build up a static charge when handled, since such static charge can cause problems such as different sample holders 10 sticking together, interfering with handling. An exemplary suitable plastics material is Acrylonitrile Butadiene Styrene (ABS). However, any other suitable plastics material could be used as an alternative.

The biological sample storage medium 11 is typically an absorbent membrane storage medium, and may be treated with chemicals to stabilise samples stored on the sample storage medium 11. Examples of suitable storage media include untreated paper such as #903® brand paper (manufactured by Whatman, Inc.), and treated filter papers, such as FTA® and FTA® Elute brand paper (also manufactured by Whatman, Inc). Examples of samples that may be stored include blood, saliva and other bodily fluids.

During assembly of the holding device, the storage medium 11 is first aligned with one of the frames 12a, 12b so that at least part of the storage medium overlaps with the window 13 of that frame 12a, 12b. Next, the other frame 12b, 12a is further aligned so that at least part of the window 13 of this second frame 12b, 12a overlaps with the storage medium 11. Typically, the second frame 12b, 12a is of the same shape and size as the first frame 12a, 12b, and is aligned so that its edges are aligned with those of the first frame 12a, 12b. Once aligned, the two frames 12a, 12b are attached to one another so that the storage medium 11 is enclosed within the frames 12a, 12b.

The frames 12a, 12b may be attached to one another using an ultrasonic welding process, in which the two frames 12a, 12b are held together, and ultrasonic vibrations are applied to the edges of the frames 12a, 12b to create a solid-state weld. Alternatively, the two frames 12a, 12b could be attached to one another, using an adhesive, for example.

Figure 1B:
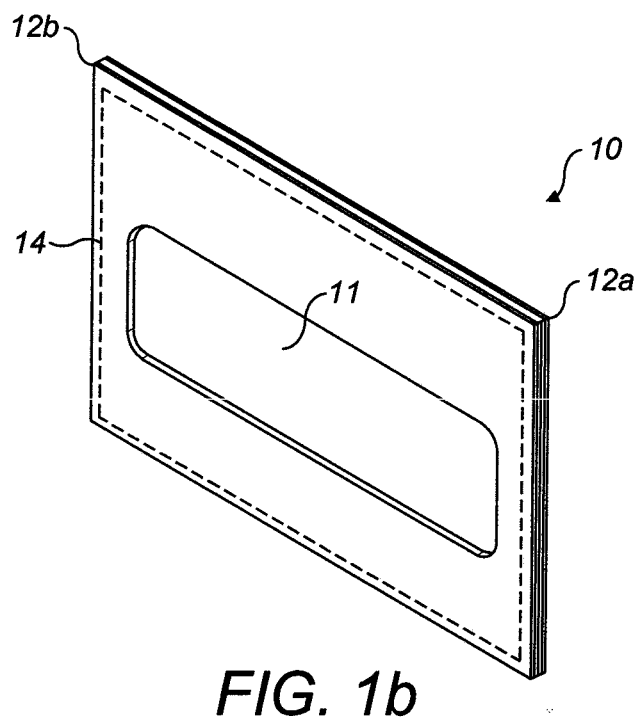
FIG. 1b shows a perspective view of a device for holding a biological sample according to the first embodiment.

FIG. 1b shows an exemplary assembled sample holder 10. An ultrasonic weld 14 along the peripheral edge of the sample holder 10 substantially permanently holds the frames 12a, 12b together such that the biological sample storage medium 11 cannot be removed. The sample storage medium 11 is accessible via the window 13 of each the first frame 12a and the second frame 12b. Aside from providing access to the sample, the windows 13 aid ventilation of the sample storage medium 11, improving drying of the sample, and also allows the sample to be easily removed during subsequent processing, by, for example "punching out" a portion of the sample storage medium 11 holding the sample.

Figure 2:
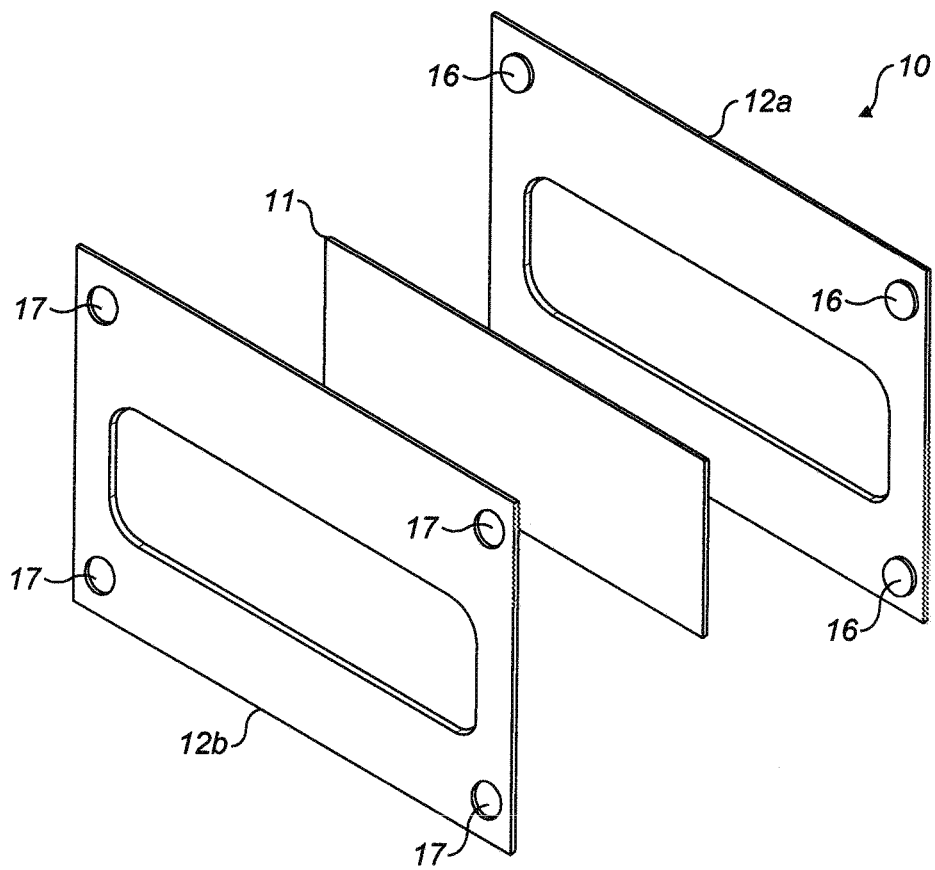
FIG. 2 shows a perspective exploded view of a device for holding a biological sample holder according to a second embodiment of the present invention.

The alignment of the frames may be facilitated by the use of bosses and holes, as shown in the embodiment of the present invention illustrated in FIG. 2. In FIG. 2, the first rigid frame 12a includes a set of four alignment bosses 16, and the second rigid frame 12b includes a corresponding set of four alignment holes 17. The bosses 16 and holes 17 are mutually positioned so that when the two frames 12a, 12b are brought together the bosses 16 fit into the holes 17. This allows correct positioning of the two frames 12a, 12b during assembly of the device and preservation of alignment of the two frames during the joining process.

Figure 3A:
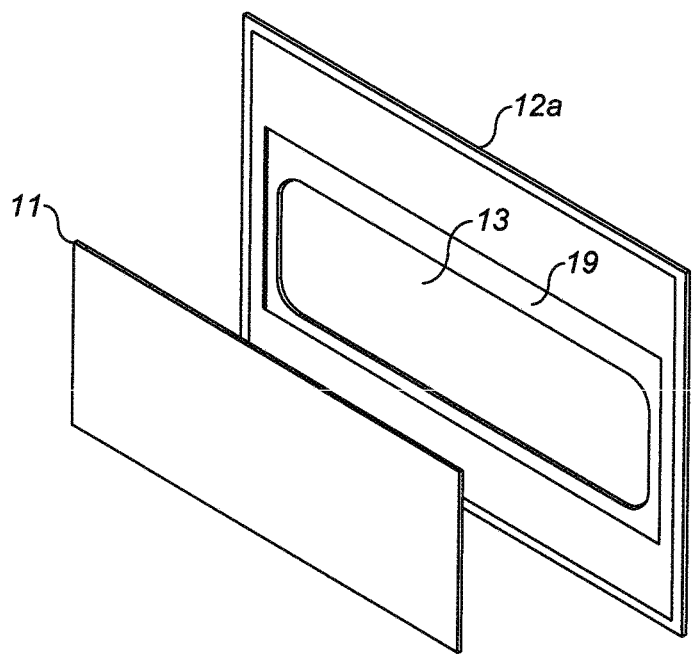
FIGS. 3a to 3c show perspective exploded views of rigid frames and biological sample holding media for assembly of a device for holding a biological sample according to third, fourth and fifth embodiments of the present invention.

In some embodiments of the invention, the holder 10 is additionally provided with means for aligning and/or holding the storage medium in the frames 12a, 12b. FIG. 3a shows an exemplary embodiment of the present invention in which edges of the window 13 in the frame 12a form a recess 19, which has dimensions corresponding to those of the sample medium 11, so that the sample medium 11 is held tightly in place during, and subsequent to, attaching of the first frame 12a to the second frame 12b. Although not shown, it will be appreciated that a corresponding recess is typically provided in the second frame 12b.

Figure 3B:
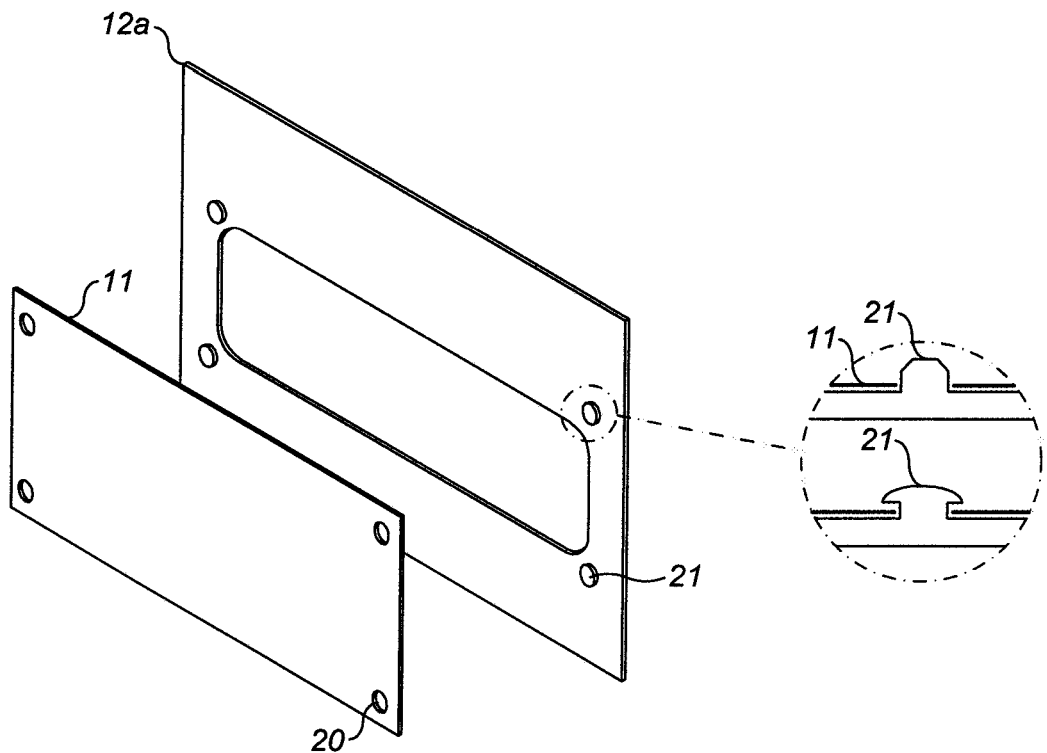

FIG. 3b shows a further embodiment of the present invention, in which a set of holes 20 are provided in the biological sample storage medium 21, and a corresponding set of stakes 21 are provided protruding from the internal surface of the frame 12a. During manufacture, the stakes 21 are positioned in the corresponding holes 20 in the biological sample storage medium 11 and heat and pressure is applied to the end of the stakes 21. This causes the ends of the stakes 21 to deform as shown in the inset to FIG. 3b such that the external diameter of the ends of each stake 21 is larger than the internal diameter of each of the holes 20. This prevents removal of the biological sample storage medium 21.

Figure 3C:
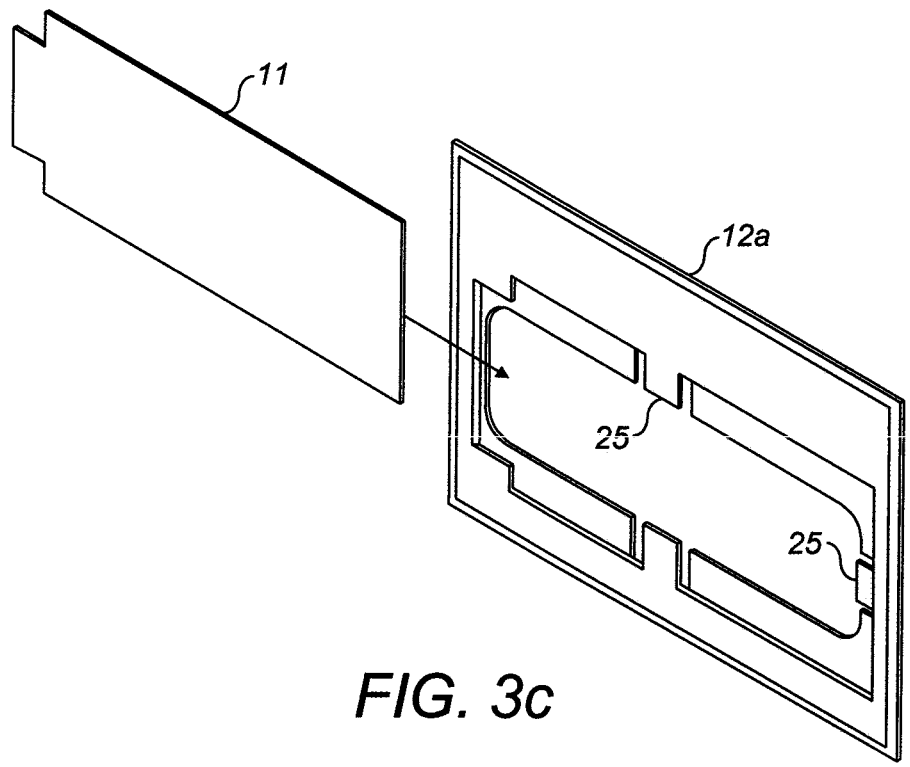

FIG. 3c shows a further embodiment of the present invention in which the frame 12a comprises a set of tabs 25 into which the sample storage medium 11 is slid and locked. This method of attaching the sample storage medium 11 to the frame 12a can be performed manually or automatically, and avoids exposing the sample storage medium 11 to heat and or pressure.

In the embodiments described with reference to FIG. 3a to FIG. 3c, the second frame 12b is typically attached to the first frame 12a subsequent to the biological sample storage medium 11 being attached to the first frame 12a as described. However, in the case of FIGS. 3b and 3c, since the biological sample storage medium 11 is permanently attached to the first frame 12a, it would also be possible to store the biological sample without using the second frame 12b, in order to reduce costs, for example.

Figure 4:
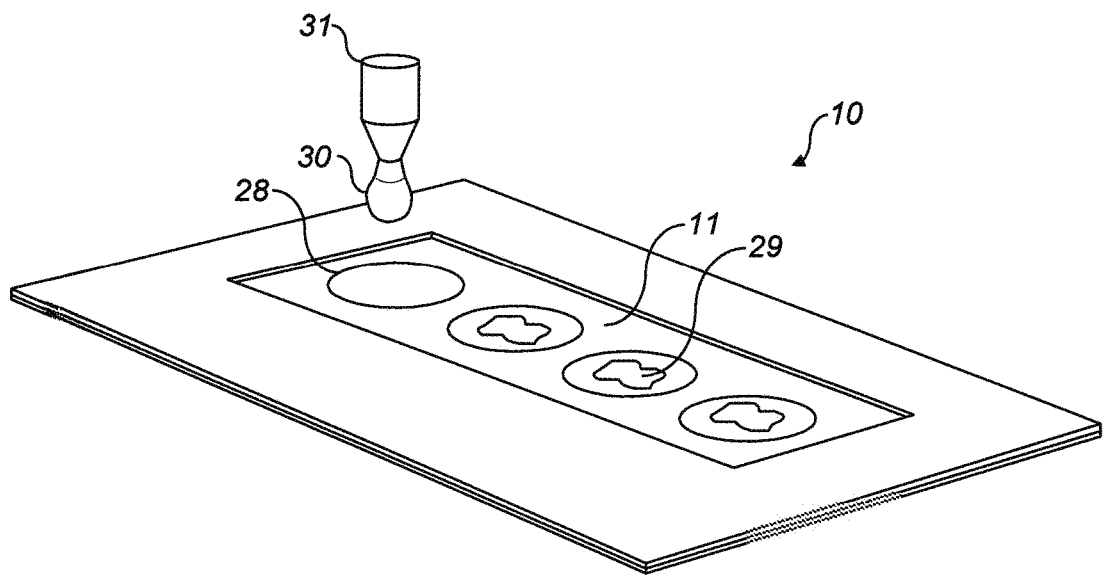
FIG. 4 shows a perspective view of a device for holding a biological sample according to a sixth embodiment of the present invention.

FIG. 4 shows an embodiment of the present invention in which a biological sample storage medium 11 includes a series of indicia, in the form of indicating marks 28 indicating positions onto which a sample 29 may be placed. The marks 28 may be printed using an ink that is not soluble in water, or in other common solvents. Typically, droplets 30 of a sample liquid are applied to the marked positions using, for example, a pipette 31, the sample being subsequently allowed to dry.

Figure 5:
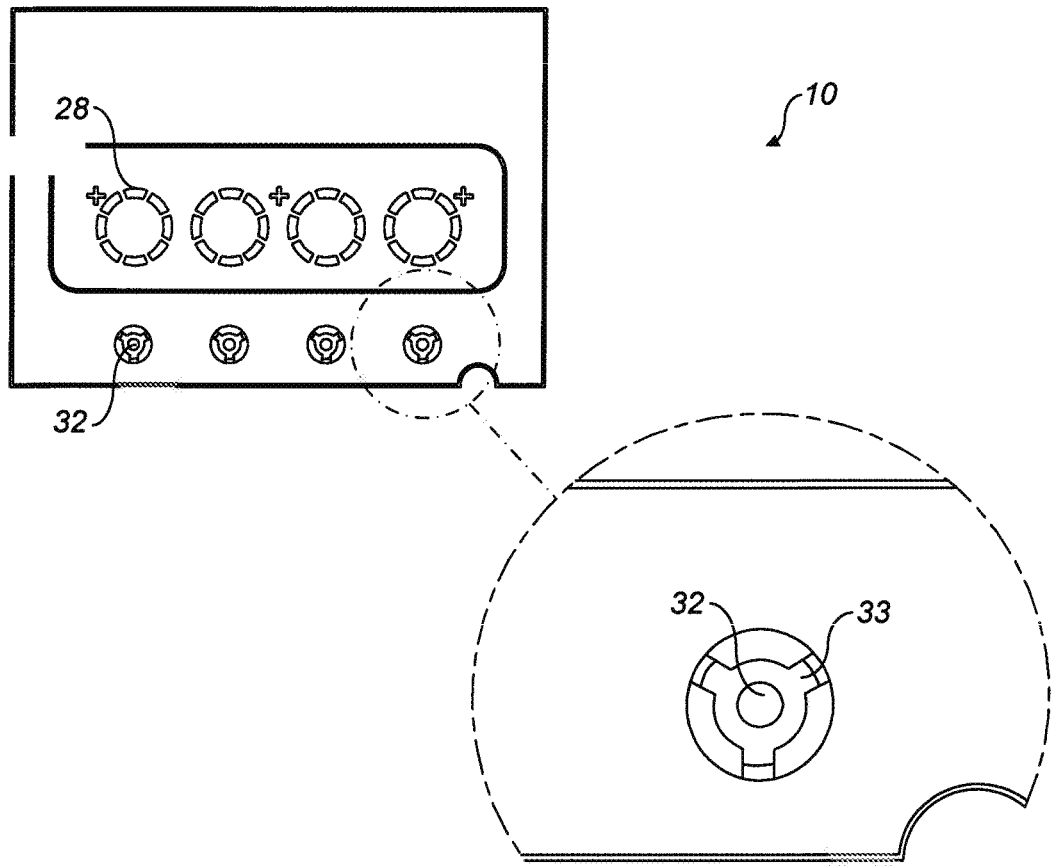
FIG. 5 shows a front view of a device for holding a biological sample according to a seventh embodiment of the present invention.

Sometimes samples may be considered unusable because, for example, they do not fall correctly within the position marking 28, or they become contaminated in some way. In order to enable a visual indication of which samples are unusable, in some embodiments of the present invention, removable tags 32 are provided in positions corresponding to the marked sample areas 28, as shown in FIG. 5. The tags 32 may be physically connected to the frames 12a, 12b by thin sprues 33 formed during the injection moulding process, such that the sprues form an area of weakness in the plastics moulded material. In this embodiment, the sprues 33 are flush with the surface of the frames 12a, 12b and are sufficiently strong to hold the tag 32 in place. However, the tags 32 may be removed by applying a small amount of pressure directly to the tag 32 when the sample is deemed unsuitable. The result is a distinct marking can be made, corresponding in alignment to the marks 28, that identifies unsuitable samples, which is visible to users and is also readable by a variety of mark-identifying equipment. Since the removal of the tag 32 is irreversible, it provides an advantage over prior art methods of indicating a bad sample in which a pen or other mark is applied to the sample holder; in these latter methods, the mark may subsequently be ignored or inadvertently removed, which could lead to unsuitable samples being used in subsequent processing.

Further, the presence, or otherwise, of a tag 32, is more easily sensed by automated machinery than the presence, or otherwise, of a pen mark.

Figure 6:
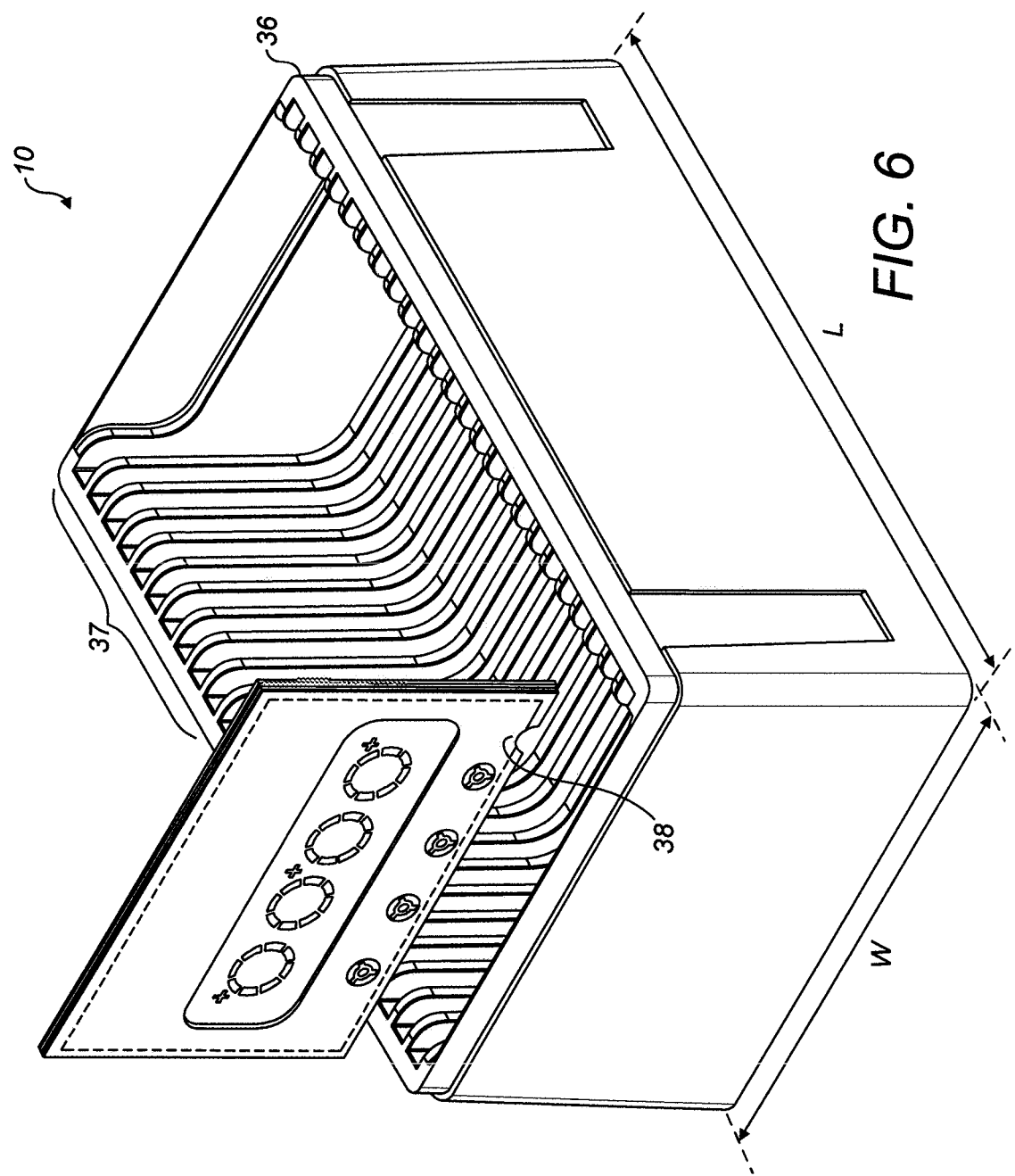
FIG. 6 shows a perspective view of a device for holding a biological sample according to an eighth embodiment of the present invention, and a magazine for storing same.

In order to automatically process high volumes of samples, it may be useful to store multiple sample holders 10 in a magazine 36 provided with multiple slots 37 for receiving the sample holder 10, as shown in FIG. 6. The rigid nature of the sample holders 10 makes it particularly suitable for this purpose. Further, in order to avoid misalignment of the card in the magazine 36, a notch 38 may be provided at an edge of the sample holder 10. A corresponding protrusion may be provided in each of the receiving slots 37 of the magazine 36, such that the sample holder 10 can only be fully inserted into the magazine 36 in one orientation e.g. so that the face of the holder 10 on which the sample is located can only face in one direction.

The magazine 36 may be arranged to conform to a standard SBS (Standard for Biomolecular Sciences) footprint, for ease of use with existing laboratory equipment. For example, the magazine 36 may have a length (L) of 127.76 mm and a width (W) of 85.48 mm.

Figure 7A:
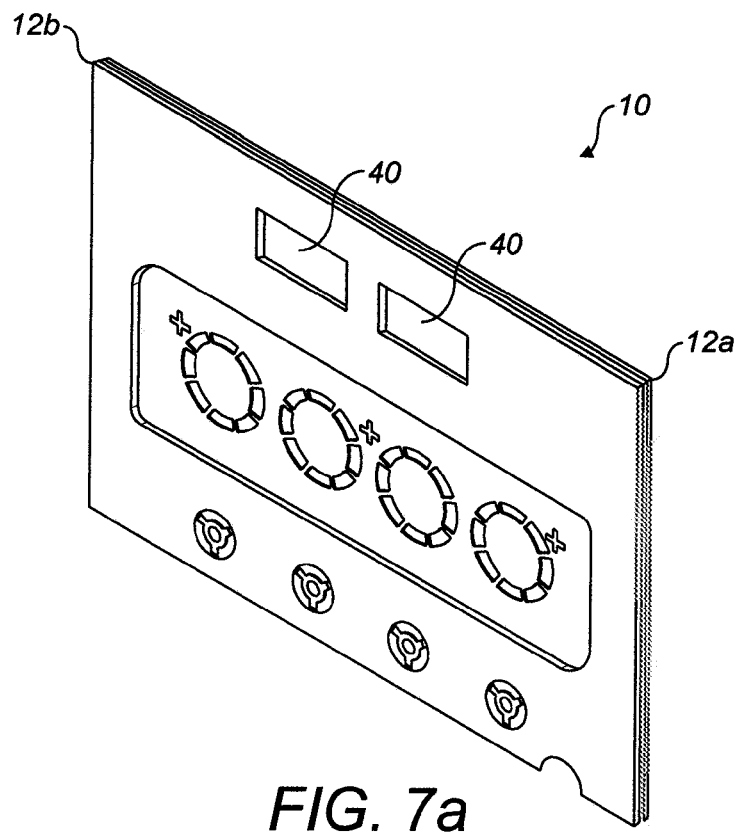
FIG. 7a shows a perspective view of a biological sample holder according to a ninth embodiment of the present invention.

FIG. 7a shows an embodiment of the present invention in which the surface of at least one of the frames 12a, 12b includes recesses 40 that correspond to the size and shape of opposing gripper fittings that often form an end effector of a robotic automated handling system. The recesses 40 allow a better grip of the frames 12a, 12b, and more accurate placement of the sample holder 35 in, for example, a testing machine and/or in a magazine 36 such as that described above with reference to FIG. 6.

Figure 7B:
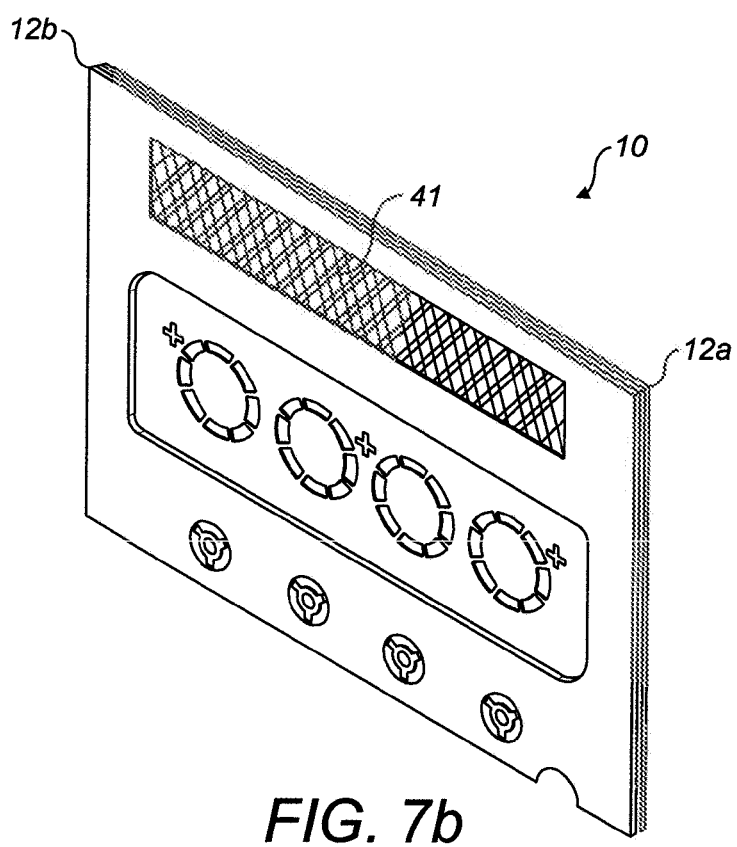
FIG. 7b shows a perspective view of a biological sample holder according to a tenth embodiment of the present invention, in which the biological sample holder is provided with a textured area for gripping during automated processing.

FIG. 7b shows an embodiment of the present invention in which a textured portion 41 is included on the surface of one or both of the frames 12a, 12b to provide additional grip. This provides an alternative means of improving handling in automated systems. The textured surface may also act as an identification aid to visually impaired people; for example, different textures could indicate different types of sample.

Figure 8:
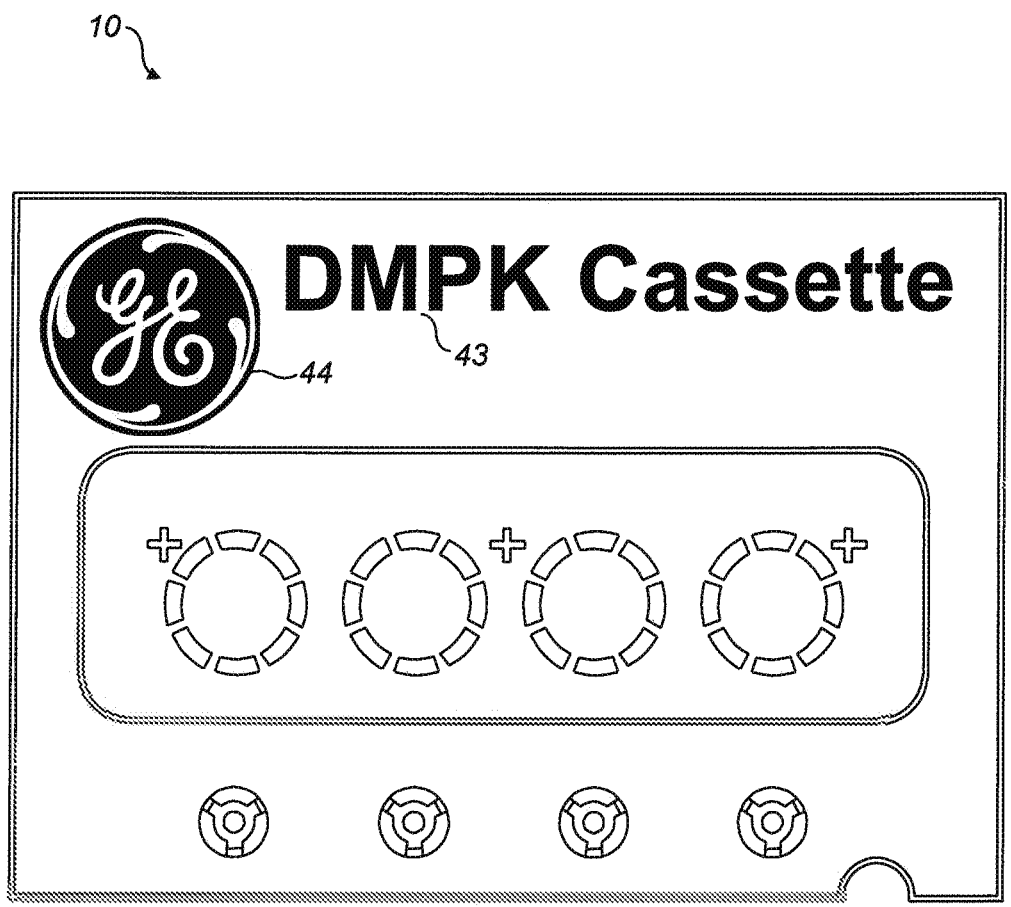
FIG. 8 shows a device for holding a biological sample according to an eleventh embodiment of the present invention.

FIG. 8 shows an embodiment of the present invention in which a printing technique, such as screen printing, is used to print textual information 43 and/or graphical information 44 on the surface of the holder 10. This information may include instructions, logos, the holder name etc. The print is typically applied in a material that is not easily removed by contact with other parts such as the magazine 36 or a robot end effector, and is not soluble in water or commonly used solvents.

Figure 9A:
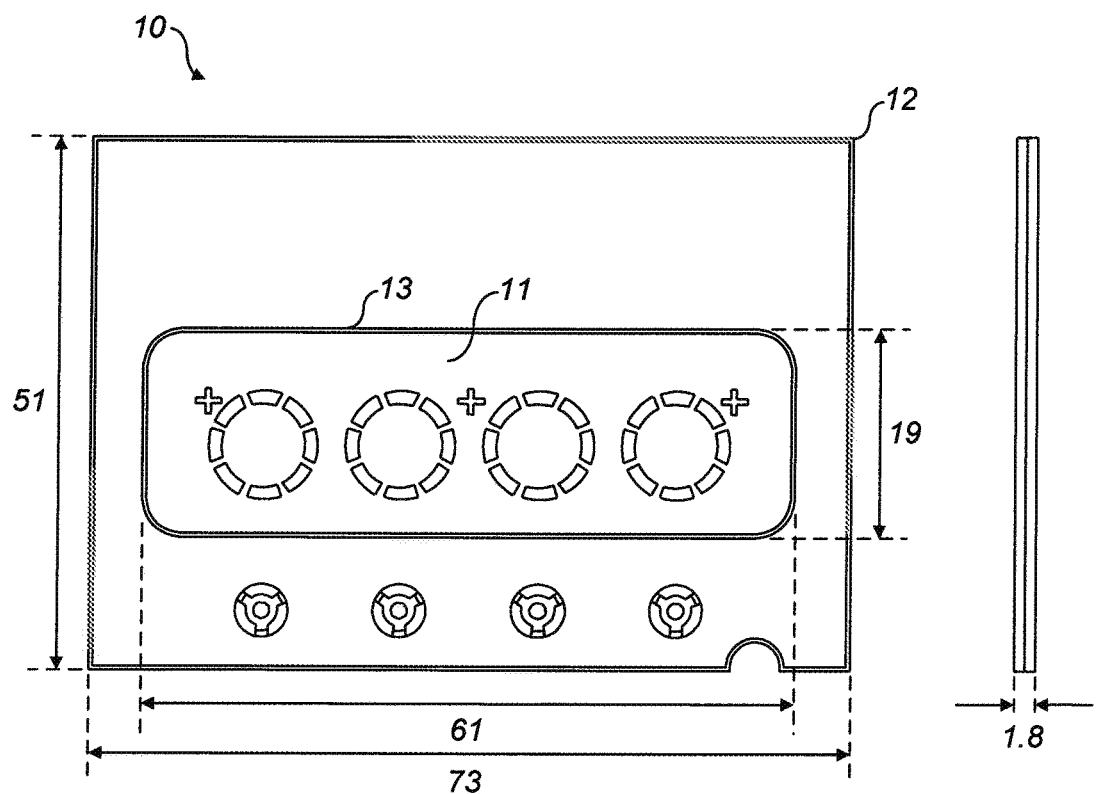
FIGS. 9a and 9b show exemplary dimensions of a device for holding a biological sample according to an embodiment of the present invention.
Figure 9B:
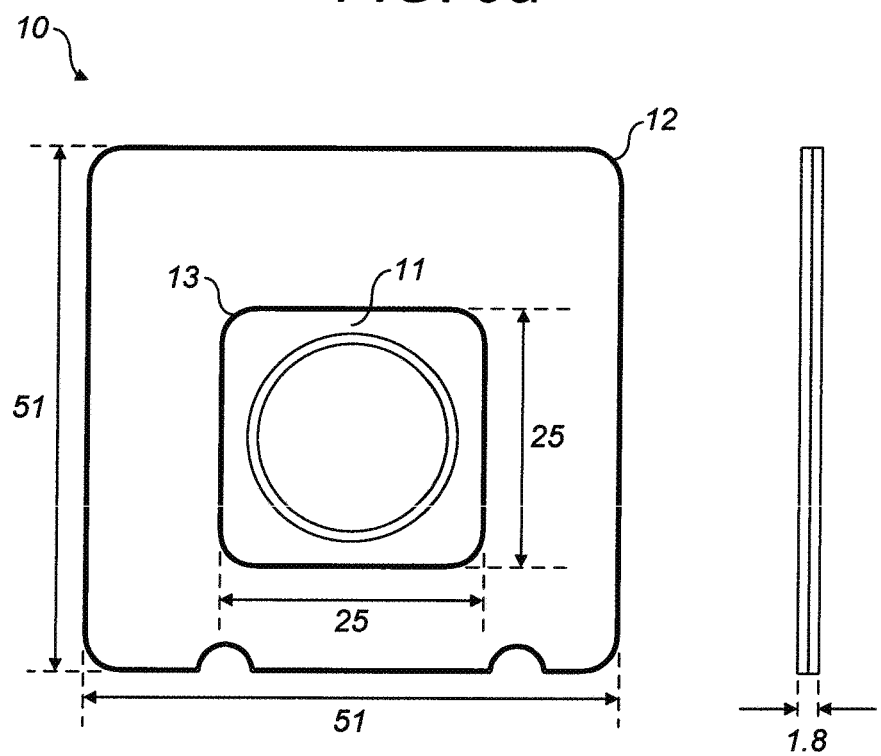

The external dimensions of the sample holder 10 may be arranged to conform to a magazine 36 having a standard SBS footprint format, as described above in relation to FIG. 6. Exemplary dimensions are shown in FIGS. 9a and 9b, the numbers shown representing millimeters.

Figure 10:
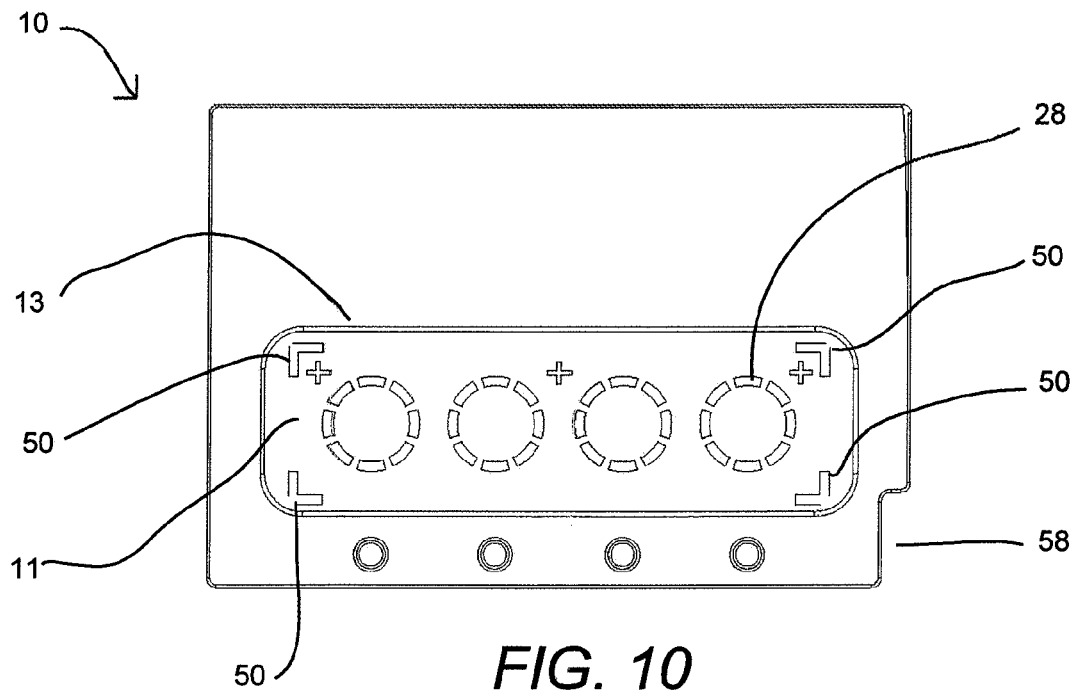
FIG. 10 shows a twelfth embodiment of an biological sample holder.

FIG. 10 shows a sample holder 10 generally as described above. In this embodiment, the previously described notch 38 is replaced by a corner notch 58 which is deeper. The corner notch 58 causes the sample holder 10 to stand above of the magazine 36 if it is inadvertently inserted incorrectly. The corner notch 58 is about 8-10 mm deep, and is deeper than the notch 38, so any upstanding of the sample holder 10 is more pronounced with this corner notch 10. This deeper notch 58 is formed at one corner of the sample holder 10 so that it is easier to manufacture the deeper notch at that location.

In addition the sample holder 10 shown in FIG. 10 has alignment marks 50 which can be recognised by image recognition software, and provide alignment for a punching mechanism (not shown) to remove a piece of the storage medium 11.

Figure 11:
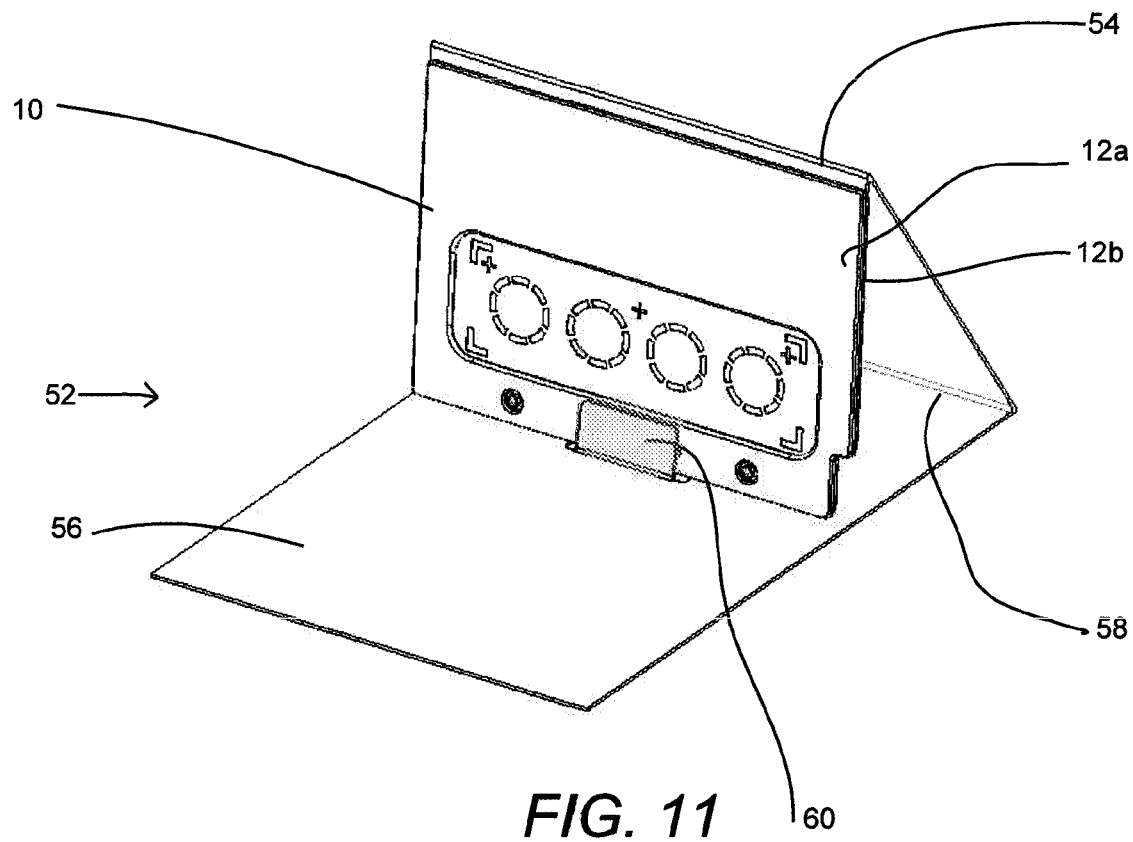
FIG. 11 shows a thirteenth embodiment of an biological sample holder.

With additional reference to FIG. 11, the sample holder 10 shown includes a protective wrapping 52, which is held at its captive end 54 between the two frame pieces 12a and 12b, and has a free end 56 which wraps around the sample holder 10 to protect it from contamination. The wrapping 52, in this case has a fold 58 for folding around the edge of the sample holder 10. In addition, the sample holder can be held by the wrapping 52 in an upstanding, drying, position as shown in FIG. 1, with the aid of a tab 60 folded away from the remainder of the wrapping 52 to keep the sample holder 10 in place.

Figure 12:
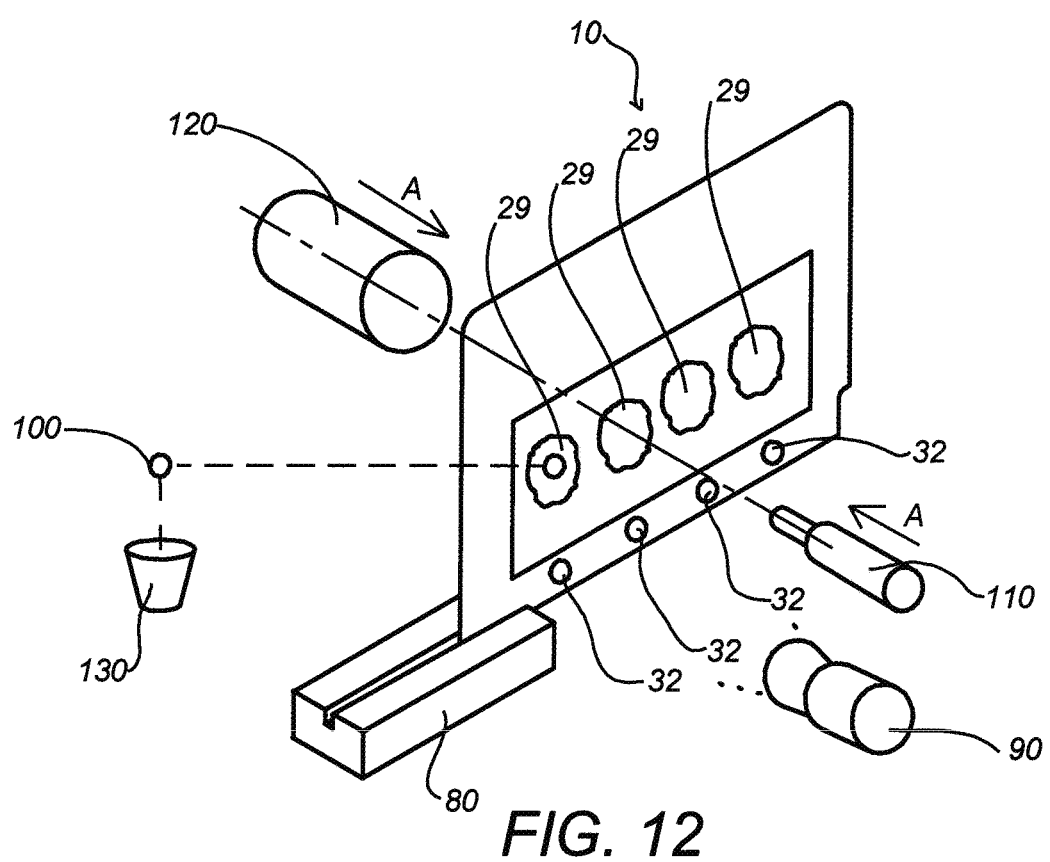
FIG. 12 shows schematically a method of analysing biological samples stored on the sample holders illustrated in the previous figures.

FIG. 12 shows a schematic representation of the processing of the biological sample 29 shown in FIG. 4. In practice, the sample holder 10 has samples 29 applied to it manually, and multiple holders 10 are loaded into a magazine 36 for automated picking. Once picked, the holder 10 is moved to a punching station 80, at which a camera 90 is used to analyse the holder 10. A moveable punch 110 accesses one side of the holder 10, and a punch backing 120 accesses the opposite side. The punch and backing which are correctly positioned by information from the camera 90, move toward each other in the direction of arrows A, to remove a sub-sample portion 100 from the holder's sample storage medium. Each sample 29 can be punched in this way as the punch and backing, move to each identified sample.

Incorrectly applied samples 29 are indicated by a removed tag 32 and the corresponding sample 29 (if it is present) is ignored.

The sub-sample 100 is treated, typically by placing the sub-sample portion 100 into a reaction chamber 130 and bio-chemically treating the sub-sample prior to its analysis, according to know techniques.

The above embodiments are to be understood as illustrative examples of the invention. Further embodiments of the invention are envisaged. For example, although it was described above that the rigid frames 12a, 12b could be manufactured using an injection moulding technique, other techniques, such as stamping from a plastic sheet could be used.

In some cases it may be desirable for the rigid frames 12a, 12b to be re-usable. In such cases, rather than the rigid frames 12a, 12b being permanently attached to one another, they could be detachably fixed together using, for example, push fasteners. In this way, when a sample storage medium 11 has been used and is no longer needed it can be removed from the frames 12a, 12b, and a new sample storage medium 11 inserted.

Further, it is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

The invention claimed is:

1. A device for holding a biological sample, the device comprising:
   a biological sample storage medium having a plurality of indicia thereon, each one of the plurality of indicia comprising indicating marks arranged to define an area onto which a biological sample can be placed and stored;
   a first rigid frame comprising a first aperture, the first aperture at least partly overlapping the biological sample storage medium; and a second rigid frame comprising a second aperture, the second aperture at least partly overlapping the biological sample storage medium, wherein the biological sample storage medium is held between the first rigid frame and the second rigid frame, wherein the biological sample storage medium is accessible via each of said first aperture and said second aperture, wherein the first frame, second frame, or a combination thereof includes a plurality of frame portions, wherein each of the plurality of frame portions correspond to a respective one of the plurality of indicia on the biological sample storage medium, wherein each of the plurality of frame portions is configured to independently indicate whether the area onto which a biological sample can be placed and stored in the respective one of the plurality of indicia is suitable for further biological sample processing, and wherein each frame portion is physically connected to and suspended within said frame by plural pre-defined areas of weakness in the frame material allowing each frame portion to be manually removed, thereby leaving an opening within the frame, said opening providing a visual indication of whether the area onto which a biological sample can be placed and stored in the respective one of the plurality of indicia is suitable for further biological sample processing.

2. The device of claim 1, wherein the biological storage medium comprises a membrane for absorbing liquid biological samples.

3. The device of claim 1, wherein at least one of the first and second rigid frames comprises a recess and said biological sample storage medium is located in said recess.

4. The device of claim 1, wherein each of the first and second rigid frames is made from a plastics material and said plural areas of weakness are each formed from a reduced thickness of said plastics material.

5. The device of claim 1, wherein each of the first rigid frame and the second rigid frame is comprised of an anti-static material.

6. The device of claim 1, wherein an outer surface of at least one of the first rigid frame and second rigid frame comprises a textured portion.

7. The device of claim 1, wherein an outer surface of at least one of the first rigid frame and second rigid frame comprises at least one recess, the at least one recess having a size and shape corresponding to that of an end effector of an automated handling system.

8. The device of claim 1, wherein each of the first and second rigid frames comprises at least one notch located on an outside edge of the frame.

9. The device of claim 8, wherein said frames are square or rectangular and said at least one notch is a portion of one or both frames removed from a corner of the square or rectangle.

10. An apparatus for storing biological samples, the apparatus comprising;
a plurality of devices of claim 8; and
a magazine comprising a plurality of slots for holding the plurality of devices of claim 8,
wherein each said slot comprises a protrusion having dimensions arranged to correspond to dimensions of said at least one notch.

11. A method for analysing biological samples, the method comprising or including the steps of:
providing a device holding the biological sample of claim 1;
accessing both sides of the biological sample storage medium of the device;
removing a portion of said biological sample storage medium during said access; and
analysing the biological content of said portion.

12. The method of claim 11, wherein the method further includes the step of:
placing a biological sample on the biological sample storage medium of the device and allowing the biological sample storage medium to dry substantially, prior to said accessing.

13. The method of claim 11, wherein said accessing and said removing steps are undertaken automatically and the removing step includes punching out the portion by directing a punch from one side of the biological sample storage medium, whilst supporting the opposite side of the medium.

14. The device of claim 1, wherein the suitability for further biological sample processing of one of the areas onto which a biological sample can be placed and stored is based on whether a biological sample falls correctly within the respective one of the plurality of indicia.

15. The device of claim 1, wherein the suitability for further biological sample processing of one of the areas onto which a biological sample can be placed and stored is based on whether a correct amount of a biological sample is applied thereto.

16. The device of claim 1, further comprising a protective wrapping, wherein the protective wrapping comprises a captive end and a free end.

17. The device of claim 16, wherein the captive end is held between the first rigid frame and the second rigid frame.

18. The device of claim 16, wherein the protective wrapping is configured to wrap around the first rigid frame, the second rigid frame, and the biological sample storage medium.

19. The device of claim 18, wherein the protective wrapping is configured to protect the biological sample storage medium from contamination.

20. The device of claim 16, wherein the protective wrapping comprises a tab.

21. The device of claim 20, wherein the tab is arranged to hold the first rigid frame, the second rigid frame, and the biological sample storage medium in an upstanding position.

* * * * *